(12) United States Patent
Sawyer et al.

(10) Patent No.: US 11,390,835 B2
(45) Date of Patent: Jul. 19, 2022

(54) GROWTH MEDIA FOR THREE-DIMENSIONAL CELL CULTURE

(71) Applicant: University of Florida Research Foundation, Inc., Gainesville, FL (US)

(72) Inventors: Wallace Gregory Sawyer, Gainesville, FL (US); Thomas Ettor Angelini, Gainesville, FL (US); Steven Craig Ghivizzani, Gainesville, FL (US); Tapomoy Bhattacharjee, Gainesville, FL (US); Glyn Daniel Palmer, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 302 days.

(21) Appl. No.: 15/571,866

(22) PCT Filed: May 7, 2016

(86) PCT No.: PCT/US2016/031385
§ 371 (c)(1),
(2) Date: Nov. 6, 2017

(87) PCT Pub. No.: WO2016/182969
PCT Pub. Date: Nov. 17, 2016

(65) Prior Publication Data
US 2018/0142194 A1 May 24, 2018

Related U.S. Application Data

(60) Provisional application No. 62/304,084, filed on Mar. 4, 2016, provisional application No. 62/159,137, filed on May 8, 2015.

(51) Int. Cl.
| | | |
|---|---|---|
| *C12M 3/00* | (2006.01) | |
| *C12N 5/00* | (2006.01) | |
| *C12M 1/12* | (2006.01) | |
| *C12M 1/42* | (2006.01) | |

(52) U.S. Cl.
CPC ............ *C12M 21/08* (2013.01); *C12M 25/14* (2013.01); *C12M 25/16* (2013.01); *C12M 35/04* (2013.01); *C12N 5/0062* (2013.01); *C12N 2513/00* (2013.01); *C12N 2527/00* (2013.01); *C12N 2533/30* (2013.01); *C12N 2535/00* (2013.01)

(58) Field of Classification Search
CPC ...... C12M 21/08; C12M 25/16; C12M 35/04; C12M 25/14; C12N 5/0062; C12N 2513/00; C12N 2527/00; C12N 2533/30; C12N 2535/00

See application file for complete search history.

(56) References Cited

U.S. PATENT DOCUMENTS

| | | | |
|---|---|---|---|
| 2,340,110 A | 1/1944 | D'Alelio | |
| 2,340,111 A | 1/1944 | D'Alelio et al. | |
| 2,533,635 A | 12/1950 | Seymour et al. | |
| 3,940,351 A | 2/1976 | Schlatzer, Jr. | |
| 4,062,817 A | 12/1977 | Westerman | |
| 4,631,557 A | 12/1986 | Cooke et al. | |
| 5,034,486 A | 7/1991 | Tzai et al. | |
| 5,034,487 A | 7/1991 | Tzai et al. | |
| 5,034,488 A | 7/1991 | Tzai et al. | |
| 5,073,491 A | 12/1991 | Familletti | |
| 5,078,994 A | 1/1992 | Nair et al. | |
| 5,284,897 A * | 2/1994 | Columbus | C09J 129/04 524/459 |
| 5,310,779 A | 5/1994 | Lai | |
| 5,349,030 A | 9/1994 | Long, II et al. | |
| 5,470,900 A | 11/1995 | Sasaki et al. | |
| 5,654,362 A | 8/1997 | Schulz, Jr. et al. | |
| 5,697,441 A | 12/1997 | Vercaemer et al. | |
| 6,279,655 B1 | 8/2001 | Pafitis et al. | |
| 6,375,880 B1 | 4/2002 | Cooper et al. | |
| 6,476,147 B1 | 11/2002 | Sullivan et al. | |
| 6,486,901 B1 | 11/2002 | Deboer et al. | |
| 6,936,212 B1 | 8/2005 | Crawford | |
| 6,942,830 B2 | 9/2005 | Muelhaupt et al. | |
| 7,049,346 B1 | 5/2006 | Van Bladel et al. | |
| 7,064,151 B1 | 6/2006 | Berge et al. | |
| 7,179,872 B2 | 2/2007 | McCormick et al. | |
| 7,285,237 B2 | 10/2007 | Newell et al. | |
| 8,133,341 B2 | 3/2012 | Nealey et al. | |
| 10,150,258 B2 | 12/2018 | Feinberg et al. | |

(Continued)

FOREIGN PATENT DOCUMENTS

| | | |
|---|---|---|
| CA | 2822487 | 7/2012 |
| CN | 1450953 | 10/2003 |
| CN | 102164661 | 8/2011 |
| CN | 203305668 U | 11/2013 |
| CZ | 26411 U1 * | 2/2014 |

(Continued)

OTHER PUBLICATIONS

Moxon, Samuel Robert, "Development of Biopolymer Hydrogels as Complex Tissue Engineering Scaffolds", Doctoral thesis, University of Huddersfield, 2016, https://pdfs.semanticscholar.org/3c17/ec0cf3598601f67db8a594436e38f456fb9c.pdf, 211 pages total, pp. I-V, pp. 1-203, (Year: 2016).*

(Continued)

*Primary Examiner* — Titilayo Moloye
(74) *Attorney, Agent, or Firm* — Thomas|Horstemeyer, LLP

(57) ABSTRACT

A three-dimensional cell growth medium is described. The cell growth medium may comprise hydrogel particles swollen with a liquid cell growth medium to form a granular gel yield stress material which undergoes a phase transformation from a solid phase to a liquid-like phase when an applied stress exceeds the yield stress. Cells may be placed in the three-dimensional cell growth medium according to any shape or geometry, and may remain in place within the three-dimensional cell growth medium.

18 Claims, 7 Drawing Sheets

(56) References Cited

U.S. PATENT DOCUMENTS

| | | | |
|---|---|---|---|
| 2004/0101518 A1 | 5/2004 | Vacanti et al. | |
| 2004/0120920 A1 | 6/2004 | Lion et al. | |
| 2004/0242837 A1 | 12/2004 | Toyoda et al. | |
| 2005/0247357 A1 | 11/2005 | Welle | |
| 2005/0282934 A1 | 12/2005 | Brinkmann et al. | |
| 2006/0136058 A1 | 6/2006 | Pietrzak | |
| 2006/0156978 A1 | 7/2006 | Lipson et al. | |
| 2006/0211790 A1 | 9/2006 | Dimotakis et al. | |
| 2009/0101271 A1 | 4/2009 | Ishida | |
| 2009/0171001 A1 | 7/2009 | Lin et al. | |
| 2009/0305412 A1* | 12/2009 | Ying | C01B 33/14 435/379 |
| 2010/0069522 A1 | 3/2010 | Linhardt et al. | |
| 2010/0102415 A1 | 4/2010 | Millward et al. | |
| 2010/0137534 A1 | 6/2010 | Magnet et al. | |
| 2010/0183977 A1 | 7/2010 | Wang et al. | |
| 2010/0184147 A1 | 7/2010 | Cheng et al. | |
| 2010/0304088 A1 | 12/2010 | Steeman et al. | |
| 2010/0321448 A1 | 12/2010 | Buestgens et al. | |
| 2010/0331232 A1* | 12/2010 | Barker | A61P 3/10 514/1.1 |
| 2011/0064810 A1 | 3/2011 | Ghanavi | |
| 2011/0103174 A1 | 5/2011 | Jung et al. | |
| 2011/0256085 A1 | 10/2011 | Talingting Pabalan et al. | |
| 2012/0040013 A1 | 2/2012 | Owens et al. | |
| 2012/0171258 A1 | 7/2012 | Sefton et al. | |
| 2013/0004385 A1 | 1/2013 | Lee et al. | |
| 2013/0029125 A1 | 1/2013 | Tse et al. | |
| 2013/0317131 A1 | 11/2013 | Scales et al. | |
| 2013/0333891 A1 | 12/2013 | Fripp et al. | |
| 2013/0344601 A1 | 12/2013 | Soman et al. | |
| 2014/0005178 A1 | 2/2014 | Kumar et al. | |
| 2014/0186952 A1 | 7/2014 | Alsberg et al. | |
| 2014/0224349 A1 | 8/2014 | Ducrée et al. | |
| 2014/0275317 A1 | 9/2014 | Moussa | |
| 2014/0295541 A1 | 10/2014 | Nakanishi et al. | |
| 2014/0037746 A1 | 12/2014 | Trefonas, III et al. | |
| 2015/0056317 A1 | 2/2015 | Chen | |
| 2015/0057786 A1 | 2/2015 | Murphy et al. | |
| 2015/0091217 A1 | 4/2015 | Araki | |
| 2015/0093465 A1 | 4/2015 | Page | |
| 2015/0104639 A1 | 4/2015 | Schroeyers et al. | |
| 2015/0022558 A1 | 8/2015 | Ohori et al. | |
| 2015/0217024 A1* | 8/2015 | Wang | A61L 27/3817 424/400 |
| 2015/0031537 A1 | 11/2015 | Mehta et al. | |
| 2016/0062230 A1 | 3/2016 | Wu et al. | |
| 2016/0106663 A1 | 4/2016 | Gulbin | |
| 2016/0167312 A1 | 6/2016 | Feinberg et al. | |
| 2016/0019689 A1 | 7/2016 | Ohori et al. | |
| 2016/0215130 A1 | 7/2016 | Esseghir et al. | |
| 2016/0235892 A1* | 8/2016 | Detamore | A61K 35/32 |

FOREIGN PATENT DOCUMENTS

| | | |
|---|---|---|
| FR | 2583334 | 12/1986 |
| FR | 2634686 | 2/1990 |
| JP | S61-98547 | 5/1986 |
| JP | 4636770 | 12/2010 |
| JP | 5167496 | 1/2013 |
| JP | 2014207886 | 11/2014 |
| WO | 0178968 | 10/2001 |
| WO | 2006027702 | 3/2006 |
| WO | 2009139395 | 11/2009 |
| WO | 2012155110 A1 | 11/2012 |
| WO | 2014024048 | 2/2014 |
| WO | 2014039825 | 3/2014 |
| WO | 2014049204 A1 | 4/2014 |
| WO | 2014182885 | 11/2014 |
| WO | 2014205261 A1 | 12/2014 |
| WO | 2014209994 | 12/2014 |
| WO | 2015017421 | 2/2015 |
| WO | 2015019212 | 2/2015 |
| WO | 2015107333 | 7/2015 |
| WO | 2015138566 | 9/2015 |
| WO | 2016044547 | 3/2016 |
| WO | 2018187595 | 10/2018 |
| WO | 2018187780 | 10/2018 |

OTHER PUBLICATIONS

Beck et al., "Enabling Surgical Placement of Hydrogels through Achieving Paste-Like Rheological Behavior in Hydrogel Precursor Solutions", Ann Biomed Eng., published online Feb. 18, 2015, 43 (10), pp. 2569-2576. (Year: 2015).*

Bhattacharjee et al., Liquid-like Solids Support Cells in 3D, ACS Biomaterials Science & Engineering, vol. 2, No. 10, p. 1787-1795, 2016.

Jin et al., Granular gel support-enabled extrusion of three-dimensional alginate and cellular structurs, Biofabrication, vol. 8, 2016.

Search Report issued by the European Patent Office for application EP16793291, dated Feb. 5, 2019.

International Search Report for PCT/US2016/031385 dated Aug. 11, 2016.

Office Action received in Japanese Patent Application No. 2017-530102 dated Oct. 29, 2019. [English translation provided].

Rudert, et al. "Experimental and numerical investigation of a viscoplastic Carbopol gel injected into a prototype 3D mold cavity," J Non-Newtonian Fluid Mechanics, 2009, vol. 161, pp. 60-68.

Khalil, et al. "Multi-nozzle deposition for construction of 3D biopolymer tissue scaffolds," Rapid Prototyping Journal, 2005, vol. 11/1, pp. 9-17.

Aldrich, S. (2019) "Thermal transitions of homopolymers: Glass transition & melting point.".

Antoni, D.; et al (2015) "Three-Dimensional Cell Culture: a Breakthrough in Vivo." International journal of molecular sciences, 16(3), pp. 5517-5527.

Baudonnet, L., J-L. ; et al. (2004) "Effect of Dispersion Stirring Speed on the Particle Size Distribution and Rheological Properties of Three Carbomers." Journal of dispersion science and technology 25.2 : 183-192.

Bayliss, K., et al. (2011) "Comparing Colloidal Phase Separation Induced by Linear Polymer and by Microgel Particles." Soft Matter 7.21 : 10345-10352.

Chang, Ya-Wen, et al. (2015) "Biofilm Formation in Geometries with Different Surface Curvature and Oxygen Availability." New Journal of Physics 17.3 : 033017.

Chinese Office Action dated Feb. 15, 2019 for Chinese Patent Application 2015800755428.

Conrad, Jacinta C; et al. (2008) "Structure of Colloidal Gels During Microchannel Flow." Langmuir 24.15 : pp. 7628-7634.

Derby, Brian. (2012) "Printing and Prototyping of Tissues and Scaffolds." Science 338.6109 : 921-926.

Ellis, Perry W., et al. (2018) "Curvature-Induced Defect Unbinding and Dynamics in Active Nematic Toroids." Nature Physics 14.1 : 85-90.

European Search Report in Appln. No. 15865693.4 dated Jul. 18, 2018.

Hardin, James O., et al. (2015) "Microfluidic Printheads for Multimaterial 3D Printing of Viscoelastic Inks." Advanced materials 27.21 : 3279-3284.

Hinton, Thomas J., et al. (2015) "Three-Dimensional Printing of Complex Biological Structures by Freeform Reversible Embedding of Suspended Hydrogels." Science advances 1.9 : e1500758.

Hinton, Thomas J., et al. (2016) "3D Printing PDMS Elastomer in a Hydrophilic Support Bath via Freeform Reversible Embedding." ACS biomaterials science & engineering 2.10 : 1781-1786.

International Search Report issued by U.S. for PCT/US2016/064771 dated Jan. 18, 2017.

International Search Report issued in European Patent Application PCT/US2016/017810 dated Jul. 12, 2016.

International Search Report dated Feb. 16, 2016 for PCT Patent Application PCT/US2015/064063.

International Search Report dated Nov. 22, 2016 for PCT Patent Application No. PCT/US2016/050175.

(56) References Cited

OTHER PUBLICATIONS

International Search Report dated Dec. 30, 2016 for PCT Patent Application No. PCT/US2016/052102.
Landers, R, et al. Desktop manufacturing of complex objects, prototypes and biomedical scaffolds by means of computer-assisted design combined with computer-guided 3D plotting of polymers and reactive oligomers. Macromolecular Materials and Engineering 2000 282(1):17-21.
Liu, Guangyao,;et al (2012) "Development of Thermosensitive Copolymers of Poly (2-Methoxyethyl Acrylate-Co-Poly (Ethylene Glycol) Methyl Ether Acrylate) and their Nanogels Synthesized by RAFT Dispersion Polymerization in Water." Polymer Chemistry 3.2 : 504-513.
Murphy, Sean V., ; et al (2014) "3D Bioprinting of Tissues and Organs." Nature biotechnology 32.8 : 773-785.
Muth, JT, et al. Embedded 3D Printing of Strain Sensors within Highly Stretchable Elastomers; 2014, 26, pp. 6307-6312, Advanced Materials; www.advmat.de.
Pairam, E., H. Le,; et al (2014) "Stability of Toroidal Droplets Inside Yield Stress Materials." Physical Review E 90.2 : 021002.
Pairam, Ekapop, et al. (2013) "Stable Nematic Droplets with Handles." Proceedings of the National Academy of Sciences 110.23 : 9295-9300.
Pfister, Andreas, et al. (2004) "Biofunctional Rapid Prototyping for Tissue-Engineering Applications: 3D Bioplotting Versus 3D Printing." Journal of Polymer Science Part A: Polymer Chemistry 42.3 : 624-638.
Rieger, J. (1996)"The Glass Transition Temperature of Polystyrene." Journal of thermal analysis 46.3-4 : 965-972.
Roberts, Geraint P., ; et al (2001) "New Measurements of the Flow-Curves for Carbopol Dispersions Without Slip Artefacts." Rheologica Acta 40.5 : 499-503.
Schaefermeier PK, et al. Design and fabrication of three-dimensional scaffolds for tissue engineering of human heart valves. Eur Surg Res. 2009 42(1):49-53.
Smith, D.,'Multi-Material Breakthrough for 3D Printing' [Press Release] The Technology Partnership, Sep. 4, 2013.
The Diamond Hotend [Product] RepRap.me: http://reprap.me/fronlpage-show/diamond-holend.hlml.
The Technology Partnership. [Relevant Business; Melbourn, UK] http://www.llp.com/printing.
Tumbleston, John R., et al.(2015) "Continuous Liquid Interface Production of 3D Objects." Science 347.6228 : 1349-1352.
Wu, Kun-Ta, et al. (2017) "Transition From Turbulent to Coherent Flows in Confined Three-Dimensional Active Fluids." Science 355.6331 : eaal1979.
Office Action received in Japanese Patent Application No. 2017-557950 dated Jan. 7, 2020. [English translation provided].

\* cited by examiner

US 11,390,835 B2

GROWTH MEDIA FOR THREE-DIMENSIONAL CELL CULTURE

RELATED APPLICATIONS

This application is the 35 U.S.C. § 371 national stage application of PCT Application No. PCT/US2016/031385, filed May 7, 2016, where the PCT claims the benefit under 35 U.S.C. § 119(e) of U.S. Provisional Patent Application Ser. No. 62/159,137, filed on May 8, 2015, and titled, "GROWTH MEDIA FOR THREE-DIMENSIONAL CELL CULTURE," and U.S. Provisional Patent Application Ser. No. 62/304,084, filed on Mar. 4, 2016, and titled, "GROWTH MEDIA FOR THREE-DIMENSIONAL CELL CULTURE MADE FROM PACKED GRANULAR HYDROGELS," each of which is incorporated herein by reference in their entireties.

GOVERNMENT SUPPORT

This invention was made with Government support under 1352043 awarded by the National Science Foundation. The Government has certain rights in this invention.

FIELD

Disclosed embodiments are related to growth media for three-dimensional cell culture.

BACKGROUND

Conventional cell culture techniques involve growing cells on a two-dimensional (2D) substrate, such as a microwell plate or a Petri dish. Such 2D cell cultures often include a growth medium disposed on the substrate to promote cell growth. However, the 2D environment of conventional cell cultures is often a poor substitute for the three-dimensional (3D) environment experienced by cells in vivo. For example, the behavior of a cell is often highly dependent on the microenvironment around the cell; in a 2D cell culture the microenvironment around the cell may be different than what a cell would experience in a 3D microenvironment.

Several techniques have been developed for 3D cell culture, including the use of hanging drop plates, magnetic levitation, or biomaterial scaffolds. However, these techniques are typically expensive and/or time consuming, and may be limited in the specific structures or geometries of tissues which may be grown and/or tested.

SUMMARY

In some embodiments, a three-dimensional cell growth medium comprises a plurality of hydrogel particles and a liquid cell culture medium. The hydrogel particles swell with the liquid cell culture medium to form a granular gel.

In some embodiments, a method for preparing a three-dimensional cell growth medium comprises mixing hydrogel particles with a liquid cell growth medium to form a granular gel. Entrained gas bubbles are removed from the granular gel.

In some embodiments, the physical properties of the three-dimensional cell growth medium can be tuned to enable the defined deposition of individual cells in a 3D fluid volume, such that their spatial position can be maintained without the need for structural support. Accordingly, embodiments may relate to cell cultures and assays using cultured cells.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

In FIG. 6a, low concentration microgels are packed to form liquid-like solids, with breakouts 1, 2, 3 showing a portion of the culture medium with decreasing resolution;

FIG. 6b illustrates that the 3D culture medium enables cell assemblies to be created (a) or isolated cells to be dispersed without significant limitations. The microgels' large mesh-size makes this medium highly permeable to nutrients, waste, and molecular reagents such as drugs, dyes, and proteins, as illustrated in FIG. 6C. A very low level of elastic stress resists the expansion of cell assemblies over time, as shown in FIG. 6d, showing changes of the cell assembly at times 1, 2 and 3. This expansion may be driven by cell proliferation or cell migration—processes that single cells can perform in liquid like solids as well, as illustrated by FIGS. 6e, f.

DETAILED DESCRIPTION

Figure 1:
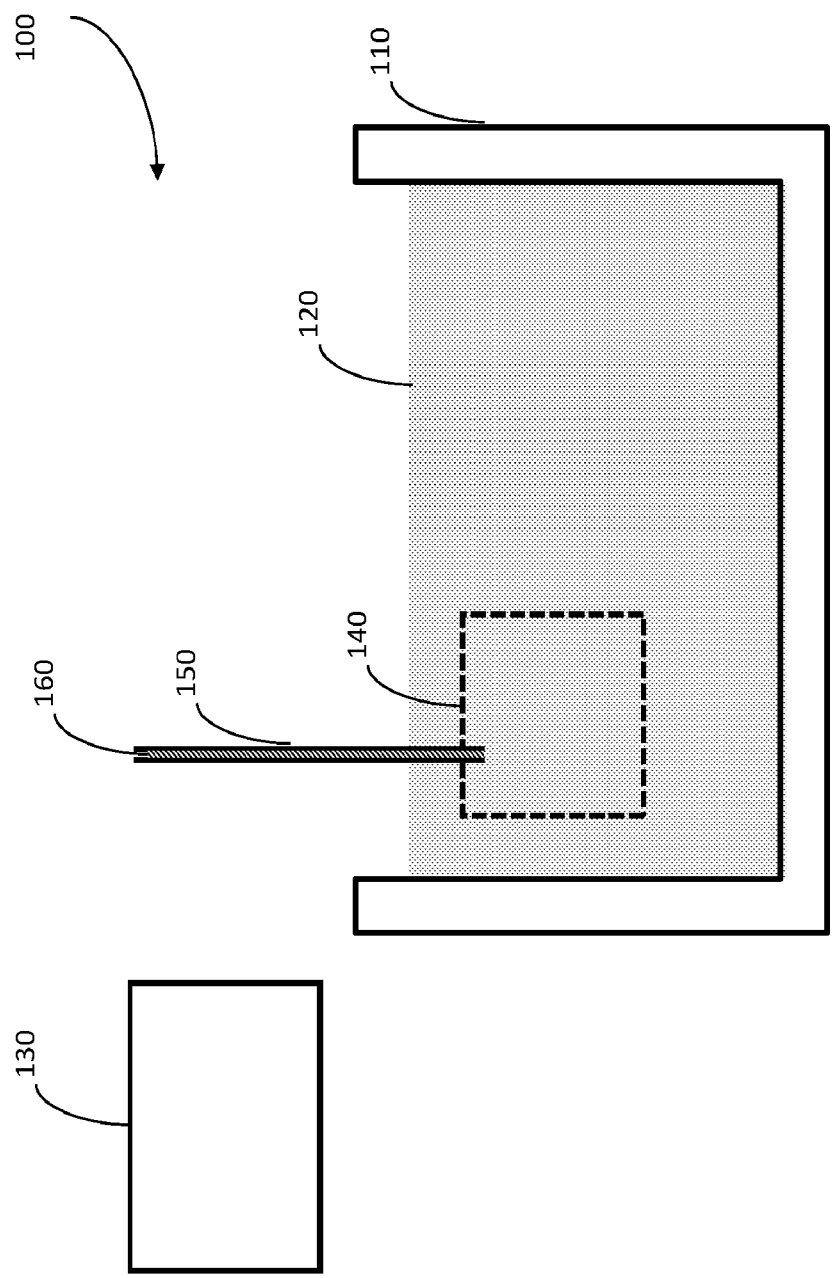
FIG. 1 is a schematic representation of one embodiment of an apparatus for placing cells in a 3D cell growth medium.

The inventors have recognized and appreciated that a 3D cell growth medium may be provided using the materials and methods described herein. The inventors have recognized and appreciated that creating a 3D growth medium using the materials described herein may allow for cell growth environment which more closely mimics the complex in vivo growth environment compared to typical 2D cell culture techniques. For example, culturing cells in a 3D culture as described herein may facilitate cell-cell interactions and the induction of biological processes, including cellular differentiation. Nonetheless, those techniques may allow for easy placement and/or retrieval of groups of cells, which may enable rapid and/or high throughput testing.

Such testing may reduce or eliminate the need for preclinical animal testing as part of new drug development. For example, may enable cancer cells to be grown in structures that mimic the dynamic environment in a cancerous tumor. Drugs may be applied to such tumors such that an indication of the efficacy of such drugs can be obtained in a fashion that is more reliable than using conventional in vitro test techniques.

Moreover, the inventors have recognized and appreciated that the 3D cell growth media described herein may allow for growing diverse cellular structures, including, but not limited to, spheroids, embryoid bodies, tumors, cysts, and microtissues, and may also be used to preserve the structure of cell-laden engineered tissue constructs.

The inventors have further recognized and appreciated that liquid-like solids (LLS) have properties that provide a combination of transport, elastic, and yielding properties, which can be leveraged to design a support material for the maintenance of living cells in three-dimensional culture. These materials may be composed predominantly of solvent that freely diffuses and can occupy more than 99% of their volume, but they also have a finite modulus and extremely low yield-stress in their solid state. Upon yielding, these materials shear and behave like classical fluids. Packed granular microgels are a class of liquid-like solids that have recently been adopted as a robust medium for precise three-dimensional fabrication of delicate materials. The unrestricted diffusion of nutrients, small molecules, and proteins can support the metabolic needs of cells and provide an easy route to the development of combinatorial screening methods. Unperturbed, LLS materials can provide support and stability to cells and to cell-assemblies, and facilitate the development and maintenance of precise multicellular structures.

Tuneable yield stress can provide a surmountable physical barrier that permits the migration, growth, and expansion of individual cells and cell-assemblies while preventing the long-term build-up of mechanical stress. The gentle yielding and rapid solidification behaviour of this culture medium allows the unrestricted placement and retrieval of cells and cell-assemblies deep within the medium. The ability of the materials to gracefully and repeatedly transition between fluidized and solid states facilitates the harvesting of selected cell groups from specific locations in space for targeted assaying. Precisely and controllably positioning and maintaining cells and cell-assemblies in 3D enables new high throughput screening methods and personalized treatment regimens to be developed with existing infrastructure and without expensive or cumbersome instrumentation.

In some embodiments, a 3D cell growth medium may comprise hydrogel particles dispersed in a liquid cell growth medium. The inventors have recognized and appreciated that any suitable liquid cell growth medium may be used; a particular liquid cell growth medium may be chosen depending on the types of cells which are to be placed within the 3D cell growth medium. Suitable cell growth medium may be human cell growth medium, murine cell growth medium, bovine cell growth medium or any other suitable cell growth medium. Depending on the particular embodiment, hydrogel particles and liquid cell growth medium may be combined in any suitable combination. For example, in some embodiments, a 3D cell growth medium comprises approximately 0.5% to 1% hydrogel particles by weight.

In accordance with some embodiments, the hydrogel particles may be made from a bio-compatible polymer.

The hydrogel particles may swell with the liquid growth medium to form a granular gel material. Depending on the particular embodiment, the swollen hydrogel particles may have a characteristic size at the micron or submicron scales. For example, in some embodiments, the swollen hydrogel particles may have a size between about 0.1 μm and 100 μm. Furthermore, a 3D cell growth medium may have any suitable combination of mechanical properties, and in some embodiments, the mechanical properties may be tuned via the relative concentration of hydrogel particles and liquid cell growth medium. For example, a higher concentration of hydrogel particles may result in a 3D growth medium having a higher elastic modulus and/or a higher yield stress.

The inventors have recognized and appreciated that such tunability may be advantageous for controlling the environment around a group of cells placed in a 3D cell growth medium. For example, a 3D cell growth medium may have mechanical properties which are tuned to be similar to those found in vivo so that the cells 3D growth medium may emulate the natural environment of the cells. However it should be understood that the mechanical properties of a 3D cell growth medium may not be similar to those found in vivo, or may be tuned to any suitable values, as the disclosure is not so limited.

According to some embodiments, a 3D cell growth medium may be made from materials such that the granular gel material undergoes a temporary phase change due to an applied stress (e.g. a thixotropic or "yield stress" material). Such materials may be solids or in some other phase in which they retain their shape under applied stresses at levels below their yield stress. At applied stresses exceeding the yield stress, these materials may become fluids or in some other more malleable phase in which they may alter their shape. When the applied stress is removed, yield stress materials may become solid again. Stress may be applied to such materials in any suitable way. For example, energy may be added to such materials to create a phase change. The energy may be in any suitable form, including mechanical, electrical, radiant, or photonic, etc.

The inventors have recognized and appreciated that providing a 3D cell growth medium made from a yield stress material, as described above, may enable facile placement and/or retrieval of a group cells at any desired location within the 3D growth medium. For example, placement of cells may be achieved by causing a solid to liquid phase change at a desired location in a region of yield stress material such that the yield stress material will flow and be displaced when cells are injected or otherwise placed at the desired location. After injection, the yield stress material may solidify around the placed cells, and therefore trap the cells at the desired location.

However, it should be appreciated that any suitable techniques may be used to deposit cells or other biological materials within the 3-D growth medium. For example, using a syringe, pipette or other suitable tool, cells may be injected into one or more locations in the 3-D growth medium. In some embodiments, the injected cells may be shaped as a pellet, such as by centrifugation. However, it should be appreciated that a 3-D growth medium as described herein enables injection of cells suspended in a liquid, which may avoid a certifugation step in conducting tests.

Regardless of how cells are placed in the medium, the yield stress of the yield stress material may be large enough to prevent yielding due to gravitational and/or diffusional forces exerted by the cells such that the position of the cells within the 3D growth medium may remain substantially constant over time. Since the cells are fixed in place, they may be retrieved from the same location at a later time for assaying or testing by causing a phase change in the yield stress material and removing the cells. As described in more detail below, placement and/or retrieval of groups of cells may be done manually or automatically.

A yield stress material as described herein may have any suitable mechanical properties. For example, in some embodiments, a yield stress material may have an elastic modulus between approximately 1 Pa and 1000 Pa when in a solid phase or other phase in which the material retains its shape under applied stresses at levels below the yield stress. In some embodiments, the yield stress required to transform a yield stress material to a fluid-like phase may be between approximately 1 Pa and 1000 Pa. In some embodiments, the yield stress may be on the order of 10 Pa, such as 10 Pa+/−25%. When transformed to a fluid-like phase, a yield stress material may have a viscosity between approximately 1 Pa s and 10,000 Pa s. However, it should be understood that other values for the elastic modulus, yield stress, and/or viscosity of a yield stress material are also possible, as the present disclosure is not so limited.

In some embodiments, the yield stress may be tuned to match the compressive stress experienced by cell groups in vivo, as described above. Without wishing to be bound by any particular theory, a yield stress material which yields at a well-defined stress value may allow indefinite and/or unrestricted growth or expansion of a group of cells. Specifically, as the group of cells grows, it may exert a hydrostatic pressure on the surrounding yield stress material; this hydrostatic stress may be sufficient to cause yielding of the yield stress material, thereby permitting expansion of the group of cells. In such embodiments, the yielding of the yield stress material during growth of a group of cells may result in the yield stress material maintaining a constant pressure on the group of cells during growth. Moreover, because a yield stress material will yield when an applied stress exceeds the yield stress, a 3D growth medium made from a yield stress material may not be able to apply a stress to a group of cells which exceeds the yield stress. The inventors have recognized and appreciated that such an upper bound on the stress applied to a group of cells may help to ensure that cells are not unnaturally constrained, damaged or otherwise altered due to the application of large compressive stresses.

According to some embodiments, a 3D growth medium made from a yield stress material may yield to accommodate excretions such as fluids or other extracellular materials from a group of cells disposed within the 3D growth medium. Without wishing to be bound by any particular theory, excretion of fluids or other materials from a group of cells may result in an increase in the pressure in the extracellular space; if the pressure exceeds the yield stress of the 3D growth medium, the 3D growth medium may yield to accommodate the excretions, and a group of cells may excrete fluids or other materials without restriction. Such an ability of a 3D growth medium to accommodate cellular excretion may allow the 3D growth medium to more closely match an in vivo environment. Moreover, the inventors have recognized and appreciated that a 3D growth medium made from a yield stress material may allow for facile removal of cellular excretions for assaying, testing, or any other suitable purpose, as described in more detail below.

A group of cells may be placed in a 3D growth medium made from a yield stress material via any suitable method. For example, in some embodiments, cells may be injected or otherwise placed at a particular location within the 3D growth medium with a syringe, pipette, or other suitable placement or injection device. In some embodiments an array of automated cell dispensers may be used to inject multiple cell samples into a container of 3-D growth medium. Movement of the tip of a placement device through the 3D growth medium may impart a sufficient amount of energy into a region around the tip to cause yielding such that the placement tool may be easily moved to any location within the 3D growth medium. In some instances, a pressure applied by a placement tool to deposit a group of cells within the 3D growth medium may also be sufficient to cause yielding such that the 3D growth medium flows to accommodate the group of cells. Movement of a placement tool may be performed manually (e.g. "by hand"), or may performed by a machine or any other suitable mechanism.

In some embodiments, multiple independent groups of cells may be placed within a single volume of a 3D cell growth medium. For example, a volume of 3D cell growth medium may be large enough to accommodate at least 2, at least 5, at least 10, at least 20, at least 50, at least 100, at least 1000, or any other suitable number of independent groups of cells. Alternatively, a volume of 3D cell growth medium may only have one group of cells. Furthermore, it should be understood that a group of cells may comprise any suitable number of cells, and that the cells may of one or more different types.

Depending on the particular embodiment, groups of cells may be placed within a 3D cell growth medium according to any suitable shape, geometry, and/or pattern. For example, independent groups of cells may be deposited as spheroids, and the spheroids may be arranged on a 3D grid, or any other suitable 3D pattern. The independent spheroids may all comprise approximately the same number of cells and be approximately the same size, or alternatively different spheroids may have different numbers of cells and different sizes. In some embodiments, cells may be arranged in shapes such as embryoid or organoid bodies, tubes, cylinders, toroids, hierarchically branched vessel networks, high aspect ratio objects, thin closed shells, or other complex shapes which may correspond to geometries of tissues, vessels or other biological structures.

According to some embodiments, a 3D cell growth medium made from a yield stress material may enable 3D printing of cells to form a desired pattern in three dimensions. For example, a computer-controlled injector tip may trace out a spatial path within a 3D cell growth medium and inject cells at locations along the path to form a desired 3D pattern or shape. Movement of the injector tip through the 3D cell growth medium may impart sufficient mechanical energy to cause yielding in a region around the injector tip to allow the injector tip to easily move through the 3D cell growth medium, and also to accommodate injection of cells. After injection, the 3D cell growth medium may transform back into a solid-like phase to support the printed cells and maintain the printed geometry. However, it should be understood that 3D printing techniques are not required to use a 3D growth medium as described herein.

The inventors have recognized and appreciated that a 3D cell growth medium made from a yield stress material may also allow for facile retrieval of groups of cells from within the cell growth medium via a reversal of the steps used to deposit the cells. For example, cells may be removed by simply moving a tip of a removal device such as a syringe or pipette to a location where a group of cells is disposed, and applying suction to draw the cells from the cell growth medium. As described above, movement of the tip of the removal device through the 3D cell growth medium may impart sufficient energy to the material to cause yielding and accommodate removal of the cells from the 3D cell growth medium. Such an approach may be used, for example, as part of a test process in which multiple cell samples are deposited in 3D growth medium. Those deposited cells may be cultured under the same conditions, but different ones of the samples may be exposed to different drugs or other treatment conditions. One or more samples may be harvested at different times to test impact of the treatment conditions on the cells.

The inventors have recognized and appreciated that in some embodiments in which cells excrete fluids or other materials into an extracellular space, the excretions may be removed from the cell growth medium with similar methods while not removing the cells. For example, the 3D cell growth medium may support the cells and keep them substantially stationary when removing cellular excretions. In some embodiments, yielded 3D cell growth medium may flow to fill in space which was previously occupied by removed cells and/or cellular excretions.

In some embodiments, a 3D cell growth medium may be used to support and/or preserve the structure of a cell-laden engineered tissue construct. For example, a tissue construct including a scaffold or other suitable structure on which a plurality of cells is disposed may be placed into a 3D cell culture medium. The 3D cell culture medium may provide support to preserve a complex structure of the tissue construct while also providing a 3D environment for cell growth which may mimic that found in vivo.

According to some embodiments, a 3D cell growth medium may be prepared by dispersing hydrogel particles in a liquid cell growth medium. The hydrogel particles may be mixed with the liquid cell growth medium using a centrifugal mixer, a shaker, or any other suitable mixing device. During mixing, the hydrogel particles may swell with the liquid cell growth medium to form a material which is substantially solid when an applied shear stress is below a yield stress, as discussed above. After mixing, entrained air or gas bubbles introduced during the mixing process may be removed via centrifugation, agitation, or any other suitable method to remove bubbles from 3D cell growth medium.

In some embodiments, preparation of a 3D cell growth medium may also involve buffering to adjust the pH of a hydrogel particle and liquid cell growth medium mixture to a desired value. For example, some hydrogel particles may be made from polymers having a predominantly negative charge which may cause a cell growth medium to be overly acidic (have a pH which is below a desired value). The pH of the cell growth medium may be adjusted by adding a strong base to neutralize the acid and raise the pH to reach the desired value. Alternatively, a mixture may have a pH that is higher than a desired value; the pH of such a mixture may be lowered by adding a strong acid. According to some embodiments, the desired pH value may be in the range of about 7.0 to 7.4, or, in some embodiments 7.2 to 7.6, or any other suitable pH value which may, or may not, correspond to in vivo conditions. The pH value, for example may be approximately 7.4. In some embodiments, the pH may be adjusted once the dissolved $CO_2$ levels are adjusted to a desired value, such as approximately 5%

In one non-limiting example, a 3D cell growth medium comprises approximately 0.2% to about 0.7% by mass Carbopol particles (Lubrizol). The Carbopol particles are mixed with and swell with any suitable liquid cell growth medium, as described above, to form a 3D cell growth medium which comprises approximately 99.3% to about 99.8% by mass cell growth medium. After swelling, the particles have a characteristic size of about 1 μm to about 10 μm. The pH of the mixture is adjusted to a value of about 7.4 by adding a strong base, such as NaOH. The resulting 3D cell growth medium is a solid with a modulus of approximately 100-300 Pa, and a yield stress of approximately 20 Pa. When a stress is applied to this 3D cell growth medium which exceeds this yield stress, the cell growth medium transforms to a liquid-like phase with a viscosity of approximately 1 Pa s to about 1000 Pa s. As described above, the specific mechanical properties may be adjusted or tuned by varying the concentration of Carbopol. For example, 3D cell growth media with higher concentrations of Carbopol may be stiffer and/or have a larger yield stress.

In another example, ae liquid like solid medium was prepared with 0.9% (w/v) Carbopol ETD 2020 polymer (Lubrizol Co.) was dispersed in cell growth media under sterile conditions. The pH of the medium is adjusted by adding NaOH until pH 7.4 is reached under the incubation condition of 37° C. and 5% CO2, and the completely formulated material is homogenized in a high-speed centrifugal mixer. Carbopol ETD 2020 swells maximally at this pH, making it suitable for cell culture applications. The gel medium was incubated at 37° C. and 5% CO2. Cells were thereafter placed in this medium using a 3D printing technique.

Figure 7:
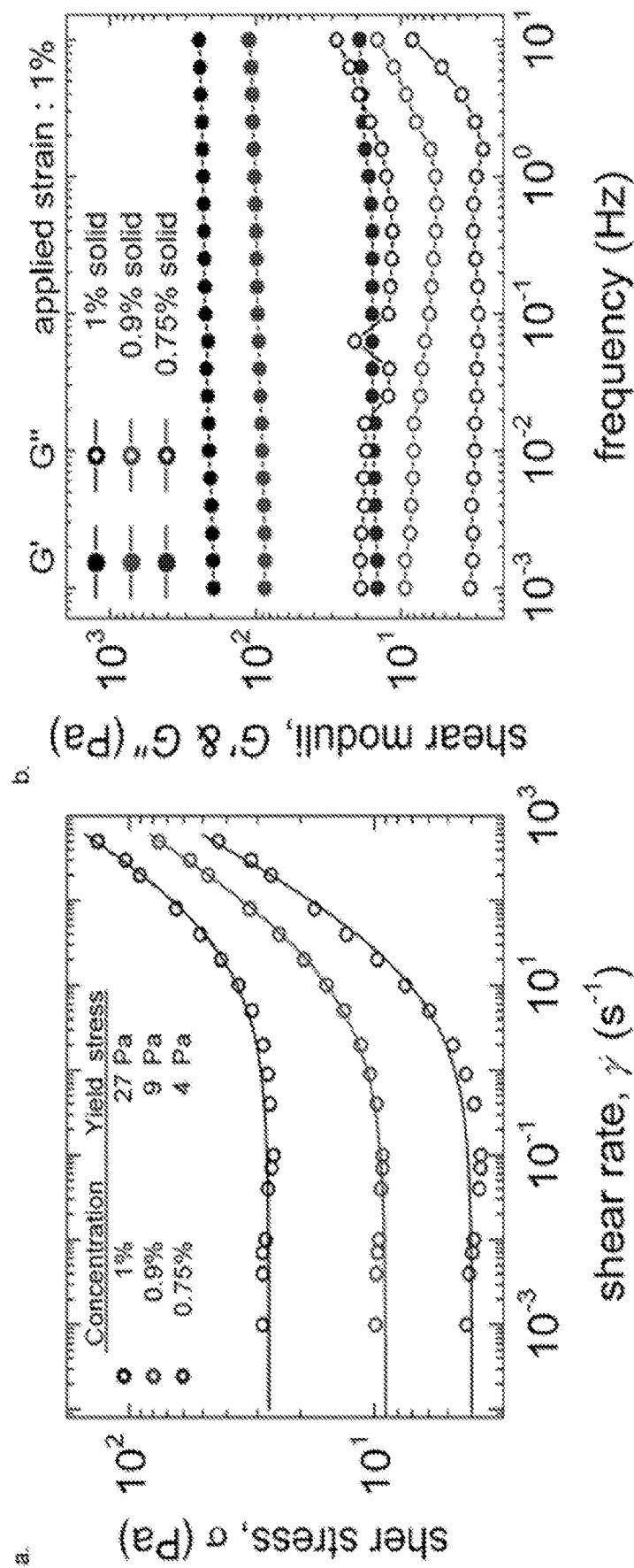
FIGS. 7a and b illustrate rheological characterization of an exemplary liquid like solid medium.

FIGS. 7a and 7b illustrate rheological characteristics of multiple exemplary LLS media. Liquid like solids at three different Carbopol concentrations were prepared as described herein. (a) The yield stress of the liquid like solid growth medium may control the quality of 3D printed cell assemblies and the support for 3D cell culture. Yield stress is measured by performing a strain rate sweep in which the stress is measured at many constant strain rates. Yield stress can be determined by fitting these data to a classic Herschel-Bulkley model ($\sigma=\sigma_y+k\dot{\gamma}^n$). (b) To determine the elastic and viscous moduli of non-yielded LLS media, frequency sweeps at 1% strain are performed. The elastic and viscous moduli remain flat and separated over a wide range of frequency, behaving like a Kelvin-Voigt linear solid with damping. Together, these rheological properties demonstrate that a smooth transition between solid and liquid phases occurs with granular microgels, facilitating their use as a 3D support matrix for cell printing, culturing, and assaying.

As should be appreciated from the discussion below, yield stress materials (i.e., materials having a Herschel-Bulkley yield stress) may be desirably used support cells, such as may be deposited in 3D printer in embodiments. As will be appreciated from the discussion below of specific yield stress materials, the inventors have recognized and appreciated the desirability, for use as support materials during 3D printing, of yield stress materials having yield stresses in a range of 1 Pascal to 1000 Pascals, and advantageously in a range of 1 to 100 Pascals or 10 to 100 Pascals. For example, embodiments are described below in which carbomer polymers (such as Carbopol®) having yield stresses between 1 and 100 Pascals are used in 3D printing. Some embodiments may operate with yield stress materials having any yield stress below 100 Pascals, with a minimum yield stress only being defined by the lower physical limit on Herschel-Bulkley yield stresses.

Separately, the inventors have recognized and appreciated the desirability of yield stress materials having a yield stress within these same ranges of 1 to 100 Pascals or 10 to 100 Pascals that are discussed below. The inventors have recognized and appreciated that, during 3D printing in a yield stress material, motion of a printing nozzle within a bath of yield stress material may create undesired (and undesirable) "crevasses" in the material. Printing in a bath of yield stress material without spontaneous formation of undesired crevasses may be avoided by using a yield stress material with a low yield stress, such as a material (like the Carbopol® materials described below) having a yield stress below 100 Pascals. For yield stress materials that are hydrogels, an upper limit on yield stress is the hydrogel's hydrostatic pressure, determined by $\rho \cdot g \cdot h$, where $\rho$ is the density of the yield stress material, g is the acceleration due to gravity, and h is a depth of printing below the surface.

For some embodiments in which living cells are being 3D printed in petri dishes and/or well plates containing a hydrogel (such as Carbopol®), the cells may be printed, for example, at a depth up to 1 cm. In such embodiments, the upper limit on yield stress (as determined from the hydrostatic pressure) is approximately 100 Pascals. Desirable hydrogel materials (including Carbopol® materials) having yield stresses up to 100 or 1000 Pascals are discussed in detail below.

Those skilled in the art will appreciate that materials having a yield stress will have certain thixotropic properties, such as a thixotropic time and a thixotropic index.

As used herein, a thixotropic time is a time for shear stress to plateau following removal of a source of shear. The inventors recognize that thixotropic time may be measured in different ways. As used herein, unless indicated otherwise, thixotropic time is determined by applying to a material, for several seconds, a stress equal to 10 times the yield stress of the material, followed by dropping the stress to 0.1 times the yield stress. The amount of time for the shear rate to plateau following dropping of the stress is the thixotropic time.

As used herein, a thixotropic index (for a yield stress material) is defined as the ratio of viscosity at a strain-rate of 2 $s^{-1}$ to viscosity at a strain-rate of 20 $s^{-1}$.

Yield stress materials with desirable yield stresses may also have desirable thixotropic properties, such as desirable thixotropic indexes or thixotropic times. For example, desirable yield stress materials (including hydrogel materials having a yield stress below 100 Pascals, some of which are described in detail below, such as Carbopol® materials) may have thixotropic times less than 2.5 seconds, less than 1.5 seconds, less than 1 second, or less than 0.5 seconds, and greater than 0.25 seconds or greater than 0.1 seconds. An exemplary Carbopol® solution may exhibit a yield stress below 100 Pascals (and below 25 Pascals in some embodiments), as well as low thixotropic times. The thixotropic times of the Carbopol® solutions having a yield stress below 100 Pascals may be less than 2.5 seconds, less than 1.5 seconds, less than 1 second, or less than 0.5 seconds, and greater than 0.25 seconds or greater than 0.1 seconds.

In some embodiments, for hydrogel yield stress materials with a yield stress below 100 Pascals (including those discussed in detail below, like Carbopol® solutions), the thixotropic index is less than 7, less than 6.5, or less than 5, and greater than 4, or greater than 2, or greater than 1.

Desirable yield stress materials, like hydrogels such as the Carbopol® solutions described herein, may thus have thixotropic times less than 2.5 seconds, less than 1.5 seconds, less than 1 second, or less than 0.5 seconds, and greater than 0.25 seconds or greater than 0.1 seconds, and/or thixotropic indexes less than 7, less than 6.5, or less than 5, and greater than 4, or greater than 2, or greater than 1.

Because of the yield stress behavior of yield stress materials, materials deposited into a yield stress material (such as through 3D printing techniques described herein) may remain fixed in place in the yield stress material, without the yield stress material or the deposited material needing to be cured or otherwise treated to reverse a phase change (e.g., by heating to cross-link, following printing). Rather, the yield stress materials permit an indefinite working time on deposition of materials inside yield stress materials, including printing of cell clusters within yield stress materials.

As should be appreciated from the foregoing, according to some embodiments, a yield stress material that may serve as a 3D construct encapsulating cells to be cultured may include one or more hydrogels. Some such hydrogels may be bio-compatible polymers. The hydrogels may be dispersed in solutions (e.g., solutions with cell growth medium) in various concentrations. One example of a concentration is below 2% by weight. Another concentration example is approximately 0.5% to 1% hydrogel particles by weight, and another is approximately 0.2% to about 0.7% by mass. Those skilled in the art will appreciate that other concentrations may be used. Those skilled in the art will further appreciate that, when disposed in a solution as discussed herein, hydrogel particles will swell with the solvent and may form a granular gel material, as discussed elsewhere herein. Such a granular gel may include swollen hydrogel particles having a characteristic size at a micron or submicron scale. For example, in some embodiments, a swollen hydrogel particle may have a size between about 0.1 µm and 100 µm, including 5 µm as discussed above.

An example of a hydrogel with which some embodiments may operate is a carbomer polymer, such as Carbopol®. Carbomer polymers may be polyelectrolytic, and may comprise deformable microgel particles.

Carbomer polymers are particulate, high-molecular-weight crosslinked polymers of acrylic acid with molecular weights of up to 3-4 billion Daltons. Carbomer polymers may also comprise co-polymers of acrylic acid and other aqueous monomers and polymers such as poly-ethylene-glycol.

While acrylic acid is a common primary monomer used to form polyacrylic acid the term is not limited thereto but includes generally all α-β unsaturated monomers with carboxylic pendant groups or anhydrides of dicarboxylic acids and processing aids as described in U.S. Pat. No. 5,349,030. Other useful carboxyl containing polymers are described in U.S. Pat. No. 3,940,351, directed to polymers of unsaturated carboxylic acid and at least one alkyl acrylic or methacrylic ester where the alkyl group contains 10 to 30 carbon atoms, and U.S. Pat. Nos. 5,034,486; 5,034,487; and 5,034,488; which are directed to maleic anhydride copolymers with vinyl ethers. Other types of such copolymers are described in U.S. Pat. No. 4,062,817 wherein the polymers described in U.S. Pat. No. 3,940,351 contain additionally another alkyl acrylic or methacrylic ester and the alkyl groups contain 1 to 8 carbon atoms. Carboxylic polymers and copolymers such as those of acrylic acid and methacrylic acid also may be cross-linked with polyfunctional materials as divinyl benzene, unsaturated diesters and the like, as is disclosed in U.S. Pat. Nos. 2,340,110; 2,340,111; and 2,533,635. The disclosures of all of these U.S. Patents are hereby incorporated herein by reference for their discussion of carboxylic polymers and copolymers that, when used in polyacrylic acids, form yield stress materials as otherwise disclosed herein. Specific types of cross-linked polyacrylic acids include carbomer homopolymer, carbomer copolymer and carbomer interpolymer monographs in the U.S. Pharmocopia 23 NR 18, and Carbomer and C10-30 alkylacrylate crosspolymer, acrylates crosspolymers as described in PCPC International Cosmetic Ingredient Dictionary & Handbook, 12th Edition (2008).

Carbomer polymer dispersions are acidic with a pH of approximately 3. When neutralized to a pH of 6-10, the particles swell dramatically. The addition of salts to swelled Carbomer can reduce the particle size and strongly influence their rheological properties. Swelled Carbomers are nearly refractive index matched to solvents like water and ethanol, making them optically clear. The original synthetic powdered Carbomer was trademarked as Carbopol® and commercialized in 1958 by BF Goodrich (now known as Lubrizol), though Carbomers are commercially available in a multitude of different formulations.

Hydrogels may include packed microgels—microscopic gel particles, ~5 μm in diameter, made from crosslinked polymer. The yield stress of Carbopol® is controlled by water content. Carbopol® yield stress can be varied between roughly 1-1000 Pa. Thus, both materials can be tuned to span the stress levels that cells typically generate. As discussed above, while materials may have yield stresses in a range of 1-1000 Pa, in some embodiments it may be advantageous to use yield stress materials having yield stresses in a range of 1-100 Pa or 10-100 Pa. In addition, some such materials may have thixotropic times less than 2.5, less than 1.5 seconds, less than 1 second, or less than 0.5 seconds, and greater than 0.25 seconds or greater than 0.1 seconds, and/or thixotropic indexes less than 7, less than 6.5, or less than 5, and greater than 4, or greater than 2, or greater than 1.

In some embodiments, silicone elastomer dispersions may also serve as yield stress materials with which some embodiments may operate.

In some embodiments, compounds may be introduced into the granular gel growth medium. Those compounds may be molecules which may be diffused throughout the granular gel or into the particles that make up the granular gel. In some embodiments, those molecules may be small molecules and/or proteins. The small molecules may be nutrients or dissolved gasses.

Turning now to the figures, specific non-limiting embodiments of 3D cell growth media and methods for their preparation and/or use are described in more detail.

FIG. 1 depicts a schematic representation of one embodiment of an apparatus 100 for placing groups of cells in a 3D cell growth medium 120. The apparatus 100 may include a container 110, a focused energy source 130, and an injector 150. The container 110 may hold the 3D cell growth medium 120. The focused energy source 130 may cause a phase change in a region 140 of the 3D cell growth medium 120 by applying focused energy to the region 140. The injector 150 may displace the 3D cell growth medium 120 with a material 160 which may include a plurality of cells.

According to some embodiments, the container 110 may be a tub, a bowl, a box, or any other suitable container for the 3D cell growth medium 120. As described above, the 3D cell growth medium 120 may include a thixotropic or yield stress material, or any material suitable for temporary phase changing. In some examples, the thixotropic or yield stress material may include a soft granular gel. The soft granular gel may be made from polymeric hydrogel particles swelled with a liquid cell culture medium. Depending on the particular embodiment, the hydrogel particles may be between 0.5 μm and 50 μm in diameter, between about 1 μm and 10 μm in diameter, or about 5 μm in diameter when swelled.

Figure 2:
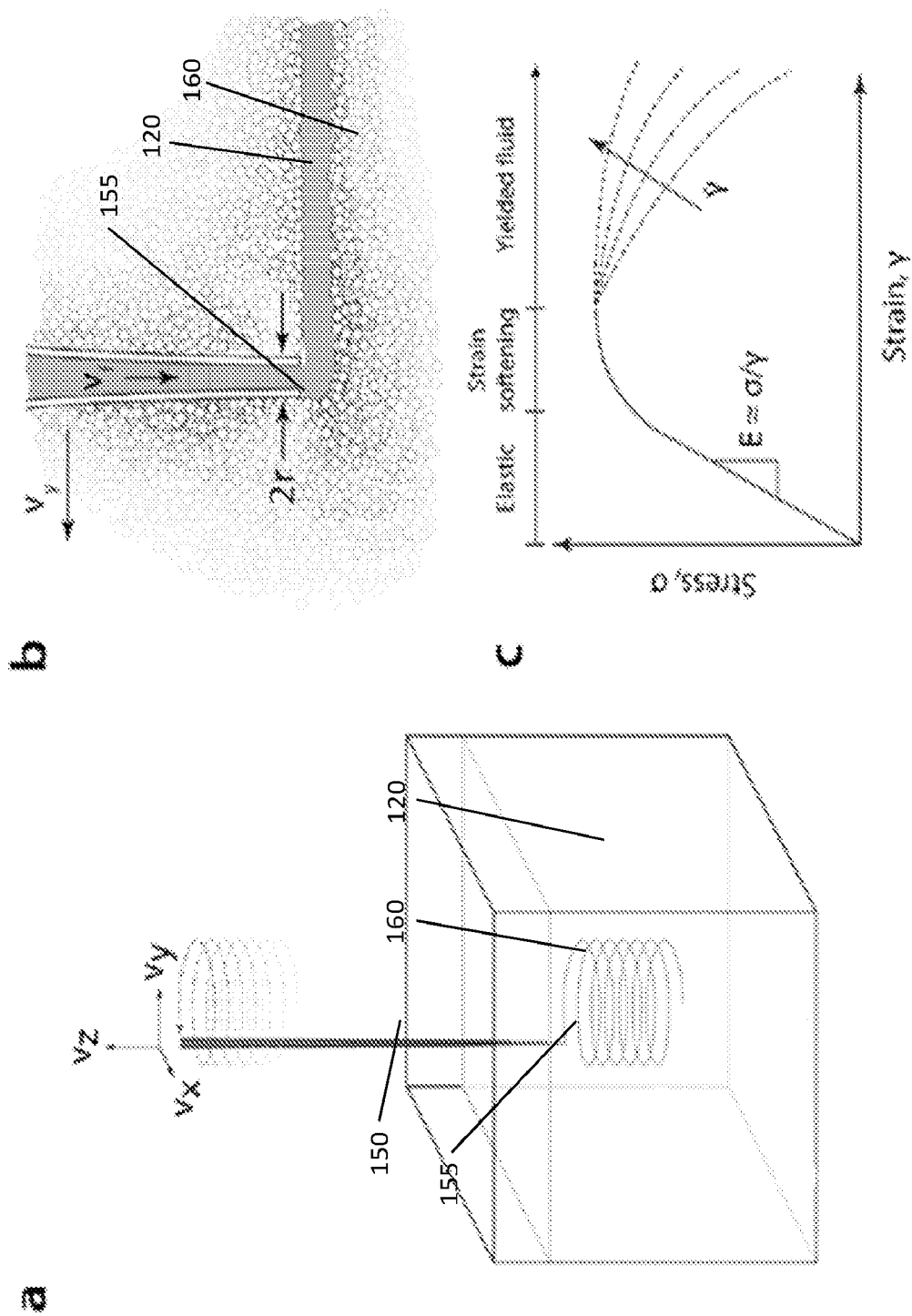
FIG. 2 illustrates (a) one embodiment of an injector placing material along a complex path in a 3D cell growth medium, (b) the tip of an injector moving through hydrogel particles, and (c) the stress-strain response of a soft granular gel.

For example, FIG. 2 illustrates (a) an injector 150 comprising a capillary with a microscale tip 155 sweeping out a complex pattern in space as a material 160 is injected into a 3D cell growth medium 120. Arbitrary aspect ratio patterns can be generated because the structure itself may not need to solidify or generate any support on its own. Additionally, FIG. 2 illustrates (b) the tip 155 traversing solidly packed hydrogel particles which comprise the 3D cell growth medium 120; movement of the tip 155 may cause the particles to fluidize and then rapidly solidify, leaving a drawn cylinder in its wake. FIG. 2 also illustrates (c) the soft granular gel medium exemplarily as a yield stress material, which may elastically deform at low shear strains, soften at intermediate strains, and fluidize at high strains.

According to some embodiments, the focused energy may include mechanical energy, such as kinetic energy due to displacement of the injector 150 relative to the first material 120. In this example, the focused energy source 130 may include the injector 150. According to some embodiments, the injector 150 may include a fine hollow tip, which may carefully trace out spatial paths within the 3D cell growth medium 120 while injecting the material 160. The movement of the tip may locally yield and fluidize the 3D cell growth medium 120 at the point of injection (i.e., in the region 140). Another example of mechanical energy may include ultrasonic pressure waves. Alternatively or additionally, the focused energy may include radiant energy, such as radio frequency radiation, which may be directed into the region 140. It should be appreciated that movement of the injector may be performed manually (e.g. "by hand") or may be automated (e.g. computer or machine controlled). Additionally or alternatively, the focused energy source 130 may cause a phase change in the region 140 of the 3D cell growth medium 120 to allow removal of material 160, including cells and or cellular excretions, as discussed above.

Figure 3:
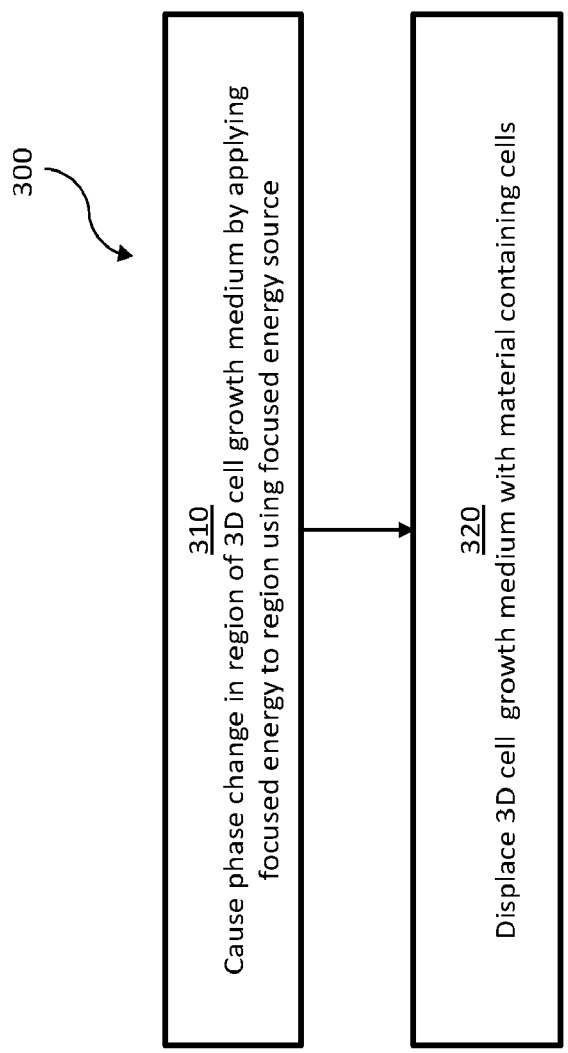
FIG. 3 is a flowchart of one embodiment of a method for placing cells in a 3D cell growth medium.

It should be appreciated from the foregoing that 3-D cell growth medium as described herein may be used in a method for three-dimensionally printing or otherwise positioning cells in a desired pattern within a 3D cell growth medium, as illustrated in FIG. 3. The method 300 begins at act 310, at which a phase change may be caused in a region of a 3D cell growth medium by applying focused energy to the region using a focused energy source. The 3D cell growth medium may be a material which may undergo a change from a less fluid to a more fluid state upon introduction of energy. In act 320, cells may be placed in the 3D cell growth medium by displacing the 3D cell growth medium with a material containing cells.

Figure 4B:
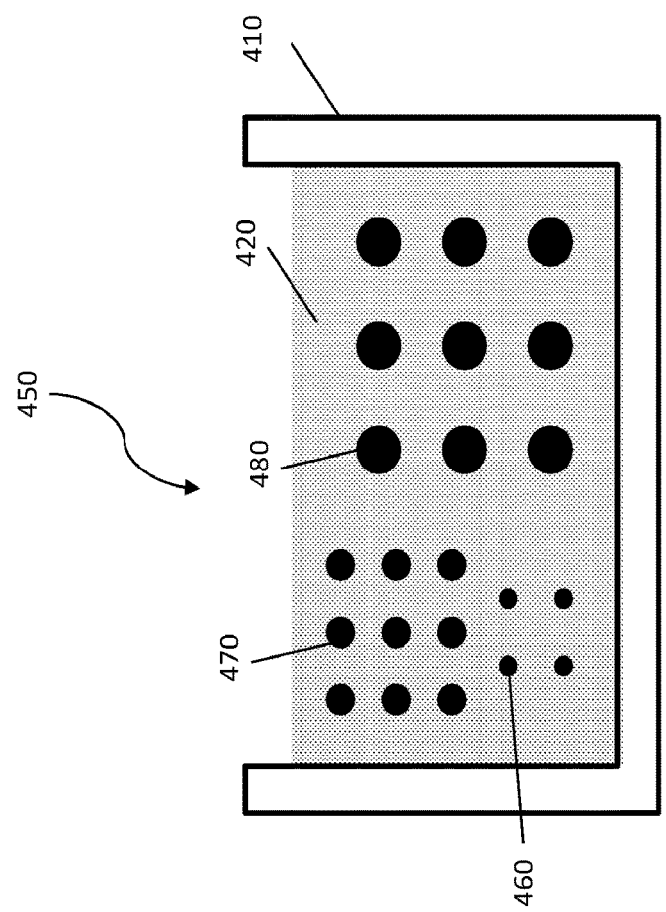
FIGS. 4A-4D are schematic representations of embodiments of a 3D cell growth medium including a plurality of cell spheroids.
Figure 4D:
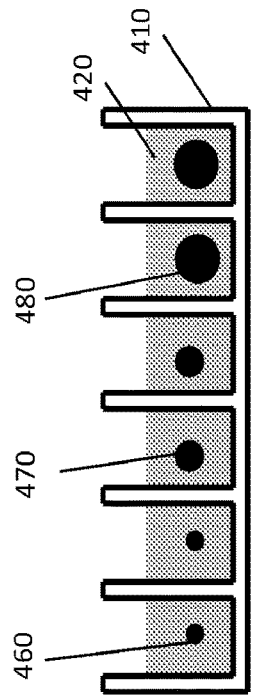
Figure 4A:
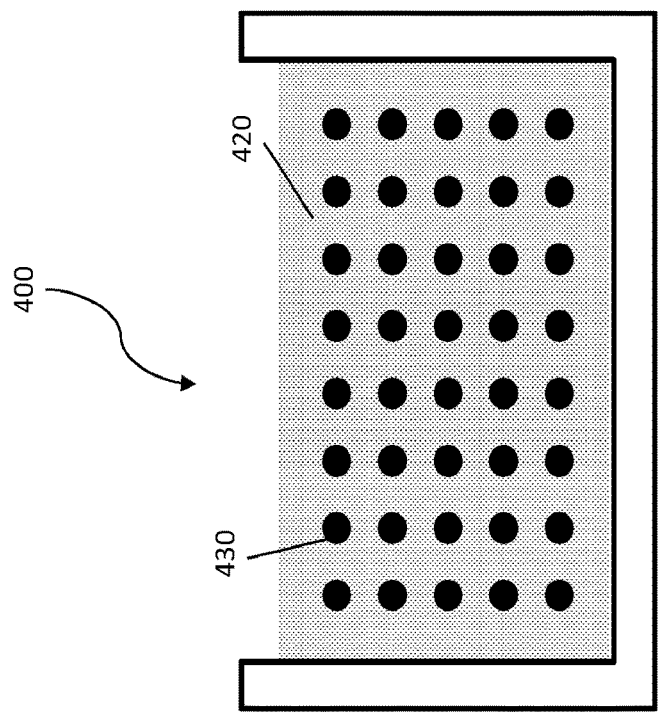

FIG. 4A depicts a cross sectional view of one embodiment of a 3D cell culture 400 including a 3D cell growth medium 420 disposed in a container 410. A plurality of spheroids 430 comprising one or more cells is arranged in the 3D cell growth medium 420. In the depicted embodiment, the spheroids 430 are approximately the same size and are spaced evenly spaced apart. In some embodiments, the spheroids may not all have the same size and/or spacing. For example, the FIG. 4B depicts another embodiment of a 3D cell culture 450 including small spheroids 460, intermediately sized spheroids 470, and large spheroids 480. In view of the above, it should be understood that cells spheroids of cells may have any suitable combination of sizes and/or spacing. Although spheroids are depicted, it should be understood that groups of cells may not be spheroid, and may be embryoid, organoid, or have any other suitable shape, as the disclosure is not so limited.

Figure 4C:
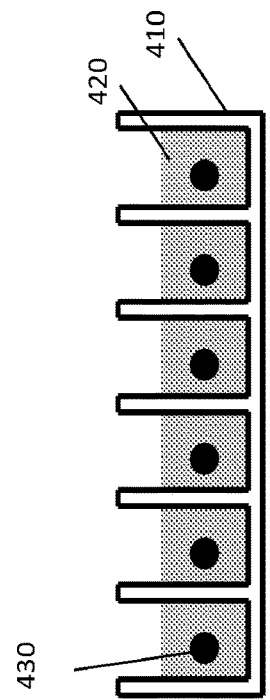

FIGS. 4A and 4B Figures illustrate the generation of multiple cell clusters, here shown as spheres, in the same vessel. FIGS. 4C and 4D illustrate the generation of multiple identical spheres or spheres of various sizes in numerous individual vessels. Vessels as illustrated may be formed in a tray 410 or other suitable carrier to facilitate high throughput testing. However, it should be appreciated, that any suitable vessel or vessels may be used.

Regardless of the type of vessel used, once the cells are deposited, the medium containing the cells may be incubated in diverse environments which may alter its chemical properties and in turn modify the growth environment of the 3D cultures contained within. For example, cells in the medium may be incubated in low oxygen or hypoxic environments.

It should be appreciated that one or more compounds may be deposited in conjunction with and/or adjacent to cells. For example, soluble, non-cellular components could be deposited in conjunction with the cells. These might include structural proteins (e.g. collagens, laminins), signaling molecules (growth factors, cytokines, chemokines, peptides), chemical compounds (pharmacologic agents), nucleic acids (e.g. DNA, RNAs), and others (nano-particles, viruses, vectors for gene transfer).

Figure 5:
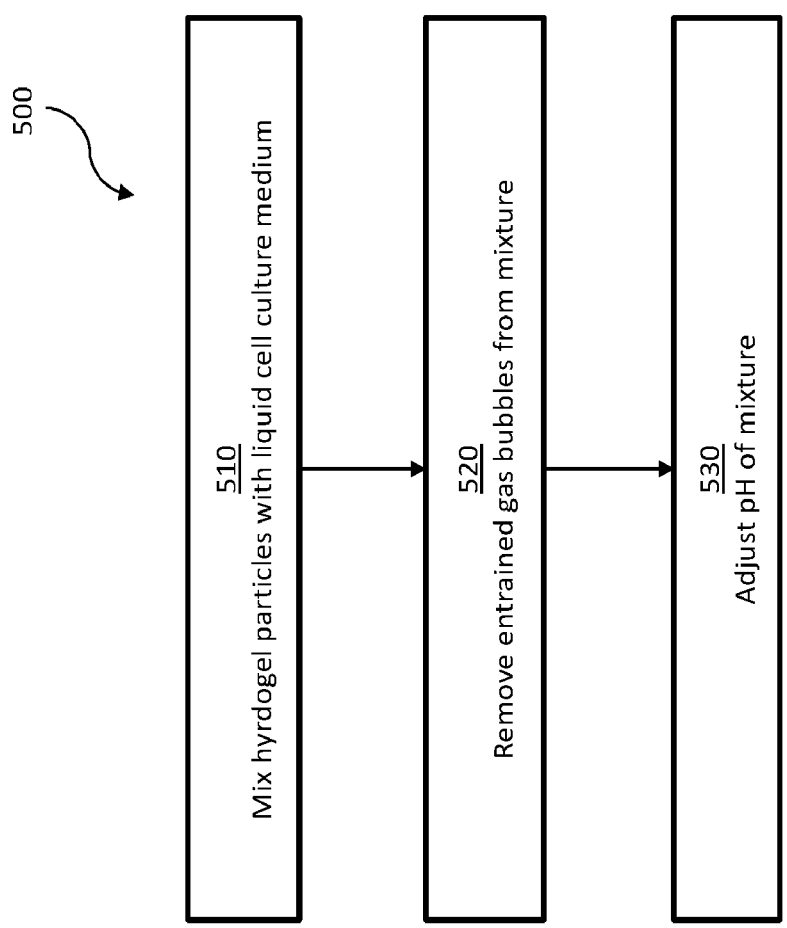
FIG. 5 is a flowchart of one embodiment of a method for preparing a 3D cell growth medium.

A method 500 for preparing a 3D cell growth medium is illustrated in FIG. 5. The method begins at act 510, at which hydrogel particles are mixed with a liquid cell culture medium. Mixing may be performed with a mechanical mixer, such as a centrifugal mixer, a shaker, or any other suitable mixing device to aid in dispersing the hydrogel particles in the liquid cell culture medium. During mixing, the hydrogel particles may swell with the liquid cell culture medium to form a granular gel, as discussed above. In some instances, the mixing act 510 may result in the introduction of air bubbles or other gas bubbles which may become entrained in the gel. Such entrained gas bubbles are removed at act 520 via centrifugation, gentle agitation, or any other suitable technique. The pH of the mixture may be adjusted at step 530; a base may be added to raise the pH, or alternatively an acid may be added to lower the pH, such until the pH of the mixture reaches a desired value. In some embodiments, the final pH value after adjustment is about 7.4.

Figure 6:
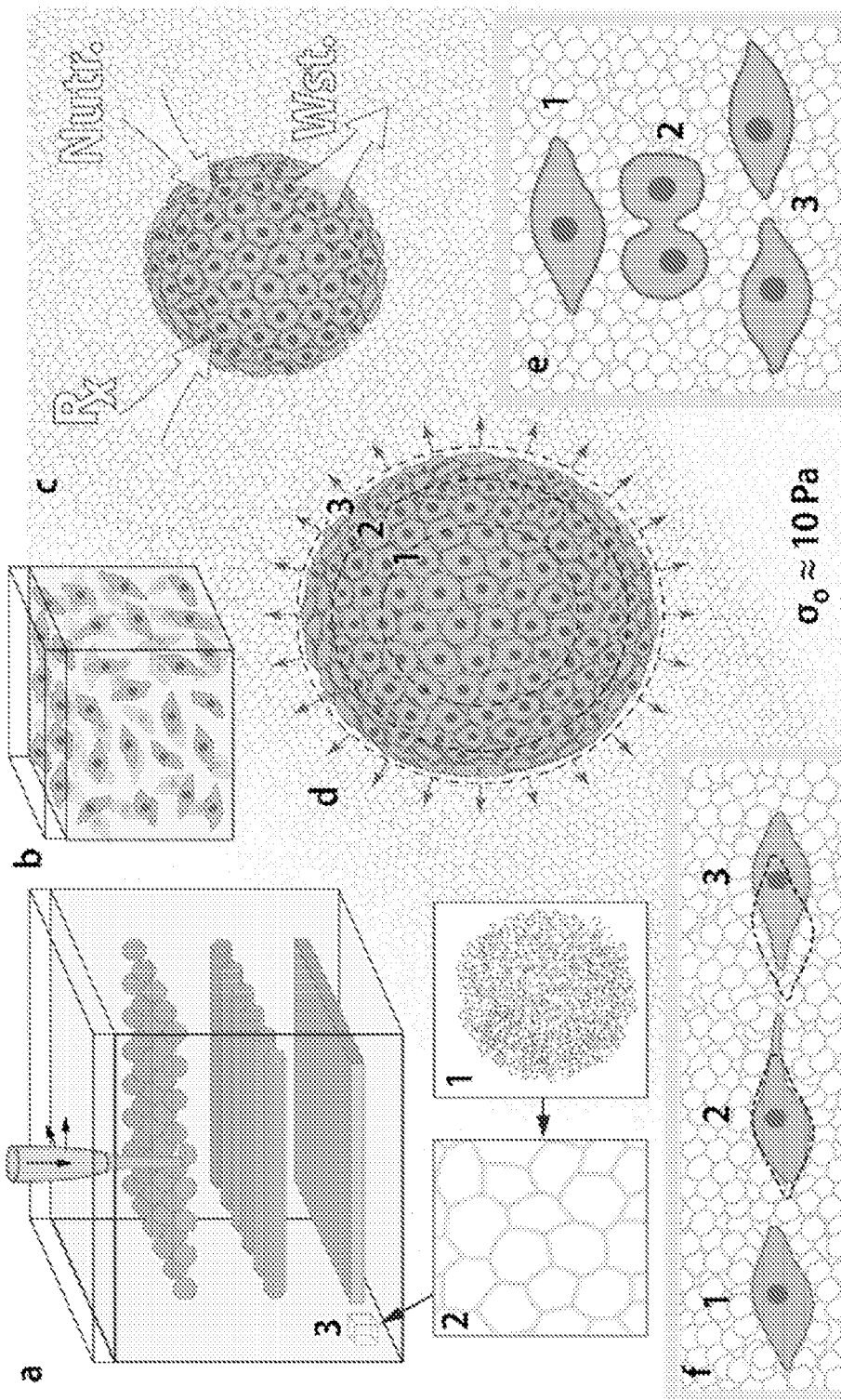
FIGS. 6a-6f are sketches illustrating an exemplary embodiment of liquid-like solids (LLS) used as 3D culture media.

FIGS. 6a-6e illustrate an example of a cell growth scenario. A barrier to culturing and studying cells in 3D is that there is no single ideal matrix for all studies. Cells thrive in natural biopolymer networks like collagen and matrigel, as well as in engineered materials with built-in motifs for adhesion and enzymatic degradation that facilitate cell migration. Unfortunately, these matrices are not designed for the precise placement and structuring of cells or for continual cell culture that uses serial passaging, harvesting, and direct assaying through fluid exchange (FIG. 6a,b). LLS made from packed microgel particles swollen with liquid cell growth medium are nearly ideally suited for these tasks; this material can be prepared from >99% (w/w) liquid growth media and can be poured into a container where it spontaneously flows and solidifies. These soft granular gels have a mesh size of approximately 100 nm, which allows for the nearly unimpeded diffusion of nutrients, waste, and small molecules (FIG. 6c), but supresses convective currents and thereby ensures that all molecular transport is diffusive. A low polymer concentration and correspondingly large mesh-size gives this LLS formulation a yield stress of about 10 Pa, which in turn sets an upper limit on the distortion stress that cells and cell assemblies experience (FIG. 6d). Such a low yield stress limits the build-up of pressure during cell migration and division (FIG. 6e,f), which may be a key contributor to long duration cell viability in 3D.

The movement of tissue cells embedded in LLS is intriguing; as a cell moves, the granular gel is displaced in the direction of travel and spontaneously flows to fill the space behind the cell. This is in sharp contrast to the migration behaviour in polymer networks, in which the 3D migration is enabled through the creation of permanent tunnels through enzymatic degradation. Our initial studies of 3D cell migration were performed by expanding cells on standard plastic tissue culture surfaces, harvesting the cells, and then manually mixing cell dispersions into the LLS 3D culture medium. These soft granular microgels are made from lightly crosslinked polyacrylic acid copolymers, which we have found to be non-cytotoxic to eight different cell types. We have found an absolute viability of about 90% after 24 hours in LLS culture of MDCK and MCF10A epithelial cells, MS1 and HAEC endothelial cells, HuH-7 hepatocytes, CTLL-2 killer T-cells, and mesenchymal stem cells. We find the same viability with primary osteosarcoma cells. 3D printed co-cultures of HuH-7 hepatocytes and MS1 endothelial cells mixed with extracellular matrix precursor showed calcein staining for two weeks and exhibited physical integrity when manually transferred between culture dishes. We have also serially passaged clusters of MCF10A cells into containers of fresh LLS growth media.

We have observed a wide range of complex behaviours that are generally thought to require anchoring in dispersed cells without the addition of natural or synthetic extracellular matrix that possesses integrin binding domains. For example, MCF10A cells extend long filapodia that tortuously explore 3D space as if navigating through an inanimate continuum of tissue, searching for receptors of other cells. These filapodia are frequently larger than the central cell body, exceeding 30 µm in length. During migration we observe cells cyclically extending directed protrusions, and then propelling their bodies forward in the same direction, leaving a trailing protrusion that finally retracts forward. In LLS with a yield stress of 10 Pa, the migration that proceeds by repeating this cycle requires the generation of protrusion forces on the order of 1 pN distributed across the cell surface at a spacing of about 300 nm, which fall well within the range of actin polymerization forces and cytoskeletal mesh-size.

Cells within tissues and networks mechanically stress their surroundings, and the LLS culture medium may provide a homogeneous continuum through which cell-cell interactions are mediated by 3D elasticity. We characterize the average degree of cell-cell interaction by the 3D tracking of cells in time and measuring the root-mean-square fluctuations in their length. We find a non-monotonic trend in this cell activity as a function of cell density. At the lowest cell densities where the cells are farthest apart, activity is low, having RMS length fluctuation on the order of 1 µm, such as between 0.05 and 51 µm, The fluctuations are also low at the highest densities, where the cells approach close packing and begin to cluster. Cell activity is maximal and greatly amplified at intermediate cell densities; at an average center-to-center cell spacing of approximately three cell diameters the cells fluctuate in length by about 100% on average. The detailed mechanism underlying this cell-cell stimulation could be chemical or mechanical. The concentration of excreted chemokine will decay sharply in 3D, as will strain fields generated by cell motion. We have observed one intriguing potential mechanism of cell-cell interaction by embedding fluorescent microspheres in the LLS and imaging the volumes around embedded fluorescent cells. We observe a thick exclusion zone around the cell body, separating the cell from the LLS by about one cell diameter (ED FIG. 5). This zone is likely filled with a pericellular matrix that many cell types produce in great abundance. Quantitative studies of the potentially diverse cell-cell interactions are facilitated by the extremely homogeneous transport and mechanical properties of granular gel based liquid-like solids, and techniques as described herein may be employed in such studies.

In accordance with another example, we observed that an LLS culture medium provides a homogeneous continuum through which cell-cell interactions are mediated by 3D elasticity, and substantially reduced the mechanical stress that cells within tissues and networks experience. We characterize the average degree of cell-cell interaction by the 3D tracking of cells in time and measuring the root-mean-square fluctuations in their length. We find a non-monotonic trend in this cell activity as a function of cell density. At the lowest cell densities where the cells are farthest apart, activity is low, having RMS length fluctuation on the order of 1 μm. The fluctuations are also low at the highest densities, where the cells approach close packing and begin to cluster. Cell activity is maximal and greatly amplified at intermediate cell densities; at an average center-to-center cell spacing of approximately three cell diameters the cells fluctuate in length by about 100% on average. The detailed mechanism underlying this cell-cell stimulation could be chemical or mechanical. The concentration of excreted chemokine will decay sharply in 3D, as will strain fields generated by cell motion. We have observed one intriguing potential mechanism of cell-cell interaction by embedding fluorescent microspheres in the LLS and imaging the volumes around embedded fluorescent cells. We observe a thick exclusion zone around the cell body, separating the cell from the LLS by about one cell diameter. This zone is likely filled with a pericellular matrix that many cell types produce in great abundance. Quantitative studies of the potentially diverse cell-cell interactions will be facilitated by the extremely homogeneous transport and mechanical properties of granular gel based liquid-like solids, and techniques as described herein may be employed for such studies.

In another example, the mechanical properties of LLS growth media was observed to enable cell division to occur with negligible physical resistance. We observe single cells dividing, during which pairs of daughter cells move apart at approximately 15 μm/h, which is comparable to the rate of cell separation in 2D culture. We estimate a strain rate for the LLS granular gel that is sheared during this step in cell division from the ratio of the separation speed, v, and the cell size, R, given by $\dot{\gamma} \equiv v/R$, which peaks at about $10^{-4}$ s$^{-1}$. Our rheological tests of the LLS during yielding show that the stress in the medium at this strain rate is the yield stress, 4-9 Pa. It should be appreciated that this value of yield stress is exemplary and materials with other yield stress, which may be achieved by altering the ration of growth medium to solid or tuning other material properties, may be in other ranges for other embodiments. For example, the yield stress may be lower, such as in the range of 1-5 Pa, or higher, such as in the range of, 7-15 Pa. Nonetheless, in this example, this value is appropriate because the cytoskeletal forces that control cell division are capable of generating much higher levels of stress than 4-9 Pa, showing that the LLS provides cradling support in 3D but does not physically impede cell division. In this example, proliferation occurs in large numbers within spheroids, where MCF10A cells have an average division time of 48 hours—about double the time found on the well plate. For cells requiring attachment through integrins or a stiffer micro-environment, natural or synthetic ECM can be mixed into the LLS medium, improving viability.

As another example, with this method we assembled primary osteosarcoma cells into forty spheroids with an average diameter of 500 μm and a standard deviation of 4.5%. The low yield stress allows the spheres to expand unimpeded over the course of eight days, during which spheroids increase in volume by 50%. Spheroids made from MCF10A cells expand at about twice this rate, while osteosarcoma spheroids 3D printed directly into dispersed killer T-cells show a decrease in volume and cell death over 22 hours. This ability to create and monitor large arrays of identical 3D micro-tissues brings another level of throughput and precision to quantitative biology.

In another example, techniques as described herein may be used for screening for the cooperative effects of multiple bio-active agents in combination, which often requires large numbers of tests that are typically performed serially. To accelerate combinatorial testing on 3D cell assemblies, spatio-temporal concentration gradients of multiple molecular species can be created with quantitative control inside of the LLS. Thus, quantitative predictions of molecular concentration profiles within the LLS are possible if boundary conditions are known. We embed time-release polymer films within the LLS to create two perpendicular boundaries that release their contents a constant rate. The films release dyes that become fluorescent by the metabolic action within living cells once absorbed. This uptake is monitored in time-lapse confocal fluorescence imaging of 3D printed arrays of HUH7 hepatocyte spheroids. We find that the integrated fluorescence signals from the two dye species in each sphere collapse onto two universal space-time scaling curves with no free parameters.

It should be understood that the embodiments of 3D cell growth media described herein are not limited to any particular types of cells. For example, various embodiments of 3D cell growth media may be used with animal, bacterial, plant, insect, or any other suitable types of cells.

Further, it should be appreciated that specific LSS formulations were provided as examples. It should be appreciated, however, that the ttransport and material properties of the LSS can be tuned by varying the polymer concentration in the LLS. For example, the concentration may be increased or decreased by 5%, 10% or more, relative to the amounts given in the examples.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

Accordingly, the foregoing description and drawings are by way of example only.

What is claimed is:

1. A three-dimensional cell growth medium comprising: a plurality of hydrogel particles; and a liquid cell culture medium, wherein the hydrogel particles are swelled with the liquid cell culture medium to form a granular gel, wherein the three-dimensional cell growth medium is a Herschel-Bulkley fluid having a yield stress less than 100 Pascals (Pa); wherein the three-dimensional cell growth medium has a yield stress such that the cell growth medium undergoes a phase change from a first solid phase to a second liquid phase upon application of a shear stress greater than the yield stress; wherein the cell growth medium comprises a plurality of cells disposed in a region of the three-dimensional cell growth medium; and wherein the three-dimensional cell growth medium maintains a spatial position of cells deposited in the three-dimensional cell growth medium.

2. The three-dimensional cell growth medium of claim 1, wherein the three-dimensional cell growth medium has a Herschel-Bulkley yield stress of 10 Pa+1-25%.

3. The three-dimensional cell growth medium of claim 1, wherein the concentration of hydrogel particles is between 0.05% to about 1.0% by weight.

4. The three-dimensional cell growth medium of claim 1, wherein the hydrogel particles have a size in the range of about 0.1 μm to about 100 μm when swollen with the liquid cell culture medium.

5. The three-dimensional cell growth medium of claim 4, wherein the hydrogel particles have a size in the range of about 1 μm to about 10 μm when swollen with the liquid cell culture medium.

6. The three-dimensional cell growth medium of claim 4, wherein the plurality of cells are arranged as at least one of spheroids, embryoid bodies, tumors, or cysts.

7. The three-dimensional cell growth medium of claim 1, further comprising molecules diffused into the granular gel particles and throughout the granular gel.

8. The three-dimensional cell growth medium of claim 7, wherein: the molecules comprise small molecules or proteins.

9. The three-dimensional cell growth medium of claim 8, wherein:
the molecules are small molecules; and
the small molecules comprise nutrients or dissolved gasses.

10. The three-dimensional cell growth medium of claim 1, wherein the three-dimensional cell growth medium has a modulus of 100-300 Pa in the first solid phase.

11. The three-dimensional cell growth medium of claim 1, wherein the three-dimensional cell growth medium has a thixotropic time less than 2.5 seconds.

12. The three-dimensional cell growth medium of claim 1, wherein the three-dimensional cell growth medium has a thixotropic time less than 1.5 seconds.

13. The three-dimensional cell growth medium of claim 1, wherein the three-dimensional cell growth medium has a thixotropic time less than 1 second.

14. The three-dimensional cell growth medium of claim 1, wherein the three-dimensional cell growth medium has a thixotropic time less than 0.5 seconds.

15. The three-dimensional cell growth medium of claim 1, wherein the three-dimensional cell growth medium has a thixotropic index less than 7.

16. The three-dimensional cell growth medium of claim 1, wherein the three-dimensional cell growth medium has a thixotropic index less than 6.5.

17. The three-dimensional cell growth medium of claim 1, wherein the granular gel has a mesh size of about 100 nm.

18. The three-dimensional cell growth medium of claim 1, wherein the plurality of hydrogel particles consist of carbomer polymers.

* * * * *